United States Patent [19]

Bitterli et al.

[11] 4,008,097
[45] Feb. 15, 1977

[54] CO-CONDENSATE MIXTURES OF IMINOISOINDOLINONES

[75] Inventors: Peter Bitterli, Reinach; Fritz Kehrer, Basel, both of Switzerland

[73] Assignee: Sandoz Ltd., Basel, Switzerland

[22] Filed: Dec. 3, 1975

[21] Appl. No.: 637,361

[30] Foreign Application Priority Data

Dec. 6, 1974 Switzerland .................. 16232/74

[52] U.S. Cl. .................. 106/288 Q; 260/325 PH; 260/37 P; 260/42.21; 106/193 P; 106/22
[51] Int. Cl.² .................. C07D 209/50
[58] Field of Search ...... 106/288 Q, 308 Q, 308 N; 260/325 PH, 326.1

[56] References Cited

UNITED STATES PATENTS

| | | | |
|---|---|---|---|
| 2,537,352 | 1/1957 | Jones | 260/325 PH |
| 3,758,497 | 9/1973 | Pugen et al. | 260/325 PH |
| 3,787,438 | 1/1974 | Thomas | 106/288 Q |
| 3,917,641 | 11/1975 | Bitterli et al. | 106/288 Q |
| 3,923,773 | 12/1975 | Ando et al. | 106/288 Q |

*Primary Examiner*—Winston A. Douglas
*Assistant Examiner*—J. V. Howard
*Attorney, Agent, or Firm*—Gerald D. Sharkin; Richard E. Vila; Joseph J. Borovian

[57] ABSTRACT

Disclosed are pigments, being co-condensate mixtures of compounds of formula I,

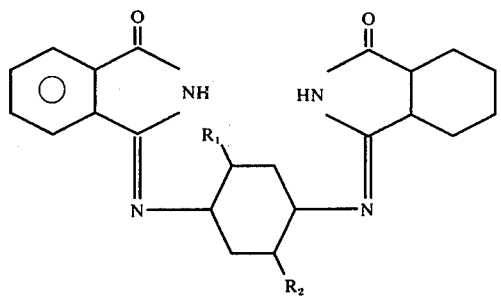

wherein
  $R_1$ is chlorine, bromine, fluorine, methyl, methoxy or ethoxy, preferably chlorine or methyl,
  $R_2$ is hydrogen or has one of the significances of $R_1$, preferably hydrogen, chlorine or methyl,
at least two of the compounds in said mixture being present in an amount of at least 0.1 mol per mol of mixture.

9 Claims, No Drawings

CO-CONDENSATE MIXTURES OF IMINOISOINDOLINONES

IMPROVEMENTS IN OR RELATING TO ORGANIC COMPOUNDS

The invention provides pigments, being co-condensate mixtures of compounds of formula I,

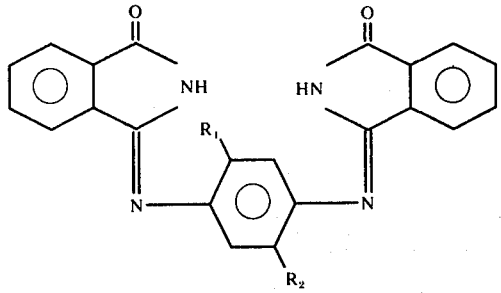

wherein $R_1$ is chlorine, bromine, fluorine, methyl, methoxy or ethoxy, preferably chlorine or methyl, $R_2$ is hydrogen or has one of the significances of $R_1$, preferably hydrogen, chlorine or methyl, at least two of the compounds in said mixture being present in an amount of at least 0.1 mol per mol of mixture.

The preferred co-condensate mixtures consist of two compounds of formula I, particularly such mixtures in which the mol % of one compound is from 20 to 70 and of the other from 80 to 30.

Particularly preferred co-condensate mixtures are of compounds (a) and (b) of formula I, as follows:

Mixture 1—(a) $R_1$ and $R_2$ are chlorine; (b) $R_1$ is chlorine and $R_2$ is hydrogen.

Mixture 2—(a) $R_1$ and $R_2$ are chlorine (b) $R_1$ is chlorine and $R_2$ is methyl.

Mixture 3—(a) $R_1$ and $R_2$ are chlorine (b) $R_1$ is methyl and $R_2$ is hydrogen.

Mixture 4—(a) $R_1$ is chlorine and $R_2$ is hydrogen (b) $R_1$ is chlorine and $R_2$ is methyl.

Mixture 5—(a) $R_1$ is chlorine and $R_2$ is hydrogen (b) $R_1$ is methyl and $R_2$ is hydrogen.

Especially preferred is the mixture 1, above, in which the mol % of component (a) is 30% and the mol % of (b) is 70% of the co-condensate mixture.

The invention also provides a process for the production of the co-condensate mixture of the compounds of formula I, which process comprises condensing a compound of formula II,

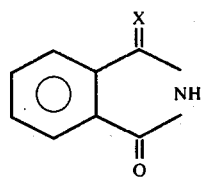

wherein $X = S$, (o-alk)$_2$ or, preferably, NH, with at least two amines of formula III,

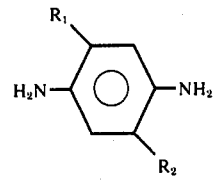

at least two of said amines being employed in an amount of at least 0.1 mol per 2 mols of the compound of formula II.

The condensation may be carried out in conventional manner.

As will be appreciated, the mol % of individual component compounds in the resulting co-condensate mixture is dependent on, and can be varied by adjusting, the mol % of the individual components in the mixture of amines of formula III.

The co-condensates of the invention after, or even without, normal pigment conditioning are useful for pigmenting a wide variety of materials, for example for in the mass pigmentation of synthetic plastics and resins such as of polyethylene, polystyrene, polyvinylchloride and synthetic leathers, with or without solvents, for the pigmentation of rubber and spun viscose and cellulose acetate, for the pigmentation of oil or water-based paints, for varnishes, lacquers and printing inks, for the pigmentation of paper in the stock and for the coating and pigment printing of textiles.

The co-condensate mixtures provided by the invention almost invariably have a greater colour strength both than the individual components in the mixtures and than simple admixtures of the components. This is believed to result from their better distribution in, for example, plastics and lacquer media.

The pigmentations produced employing the co-condensate mixtures of the invention show good migration and light fastness as well as fastness to over-varnishing. They also have good transparency and heat resistance properties.

The following Examples, in which all parts and percentages are by weight, unless otherwise stated, and in which all temperatures are in degrees Centigrade, illustrate the invention.

EXAMPLE 1

A mixture consisting of 5,3 parts 2,513 -dichloro-1,4-diaminobenzene and 10 parts 2-chloro-1,4-diaminobenzene (in a molar ratio of 30:70) is suspended in 300 parts trichlorobenzene and formed into a fine suspension by the introduction of 7,3 parts hydrogen chloride gas. 32 Parts 3-iminoisoindolinone are then added. The whole is heated to 150° and stirred for 16 hours at this temperature. The yellow pigment precipitate which forms is filtered off at 100°, washed in succession with hot trichlorobenzene, methanol and water and dried at 100°. After pulverising in a laboratory mill (or, for example, even in a coffee grinder) the pigment mixture obtained is suitable for dyeing plastics and varnishes. The dyeings have notable fastness to light, heat, migration and varnishing and, in addition, their depth of colour is 25–30% higher than from a homogeneous pigment produced from 1 mol 2,5-dichloro-1,4-diaminobenzene and 2 mols 3-imino-isoindolinone.

Compared with a homogeneous pigment produced from 1 mol 2-chloro-1,4-diaminobenzene and 2 mols 3-iminoisoindolinone, the dyeings obtained with the pigment mixture in Example 1 have an approximately 10% greater depth of colour and a significantly better resistance to heat. Moreover, there is no blooming when the mixture is used for dyeing plastics.

Application Example 0.5 Parts of the pigment mixture according to Example 1 and 5 parts titanium dioxide are added to a basic mixture consisting of
63 parts polyvinyl chloride (emulsion-type)
32 parts dioctyl phthalate,
3 parts commercial epoxy softener
1.5 parts stabiliser (barium-cadmium complex, likewise commercial grade) and
0.5 parts of a chelate former (commercial)
and the whole is intimately mixed.

To achieve better distribution of the pigment, the mixture is treated for 8 minutes on a roller frame heated to 160° and equipped with friction rollers (one operating at 20 r.p.m. and the other at 25 r.p.m.). The 0.3-mm. thick sheet obtained, which is yellow in colour, is then removed. The dyeing has notable depth of colour, is notably fast to light, migration and heat.

In the following Table A is given the relative colour strengths of co-condendates produced in analogy with Example 1 but varying the mol % of the diamines employed. Also given are the relative colour strengths obtained using the individual components of the co-condensate mixture (mol % of diamine I = 100 and mol % of diamine II = 100).

Table A

| Diamine I | : | 2,5-dichloro-1,4-diaminobenzene, |
| Diamine II | : | 2-chloro-1,4-diaminobenzene, |

| No. | Mol ratio in % I : II | | Relative colour strength in % Polyvinyl-chloride | Alkydmelamine lacquer | Polyurethane |
|---|---|---|---|---|---|
| 1 | 100 | — | 100 | 100 | 100 |
| 2 | 70 | 30 | 96 | 102 | 106 |
| 3 | 60 | 40 | 107 | 103 | 105 |
| 4 | 50 | 50 | 117 | 114 | 121 |
| 5 | 40 | 60 | 116 | 121 | 128 |
| 6 | 30 | 70 | 124 | 123 | 129 |
| 7 | 20 | 80 | 117 | 114 | 116 |
| 8 | — | 100 | 90 | 96 | 94 |

In the following Tables B to D are given the results obtained in like manner to as in Table A but employing different diamines and mixtures.

Table B

| Diamine I | : | 2,5-dichloro-1,4-diaminobenzene |
| Diamine II | : | 2-chloro-5-methyl-1,4-diaminobenzene |

| No. | Mol ratio in % I : II | | Relative colour strength in % Polyvinyl-chloride | Alkydmelamine lacquer | Polyurethane |
|---|---|---|---|---|---|
| 1 | 100 | — | 100 | 100 | 100 |
| 2 | 90 | 10 | 103 | 114 | 123 |
| 3 | 80 | 20 | 104 | 109 | 124 |
| 4 | 70 | 30 | 136 | 130 | 135 |
| 5 | 60 | 40 | 160 | 144 | 144 |
| 6 | 50 | 50 | 135 | 138 | 152 |
| 7 | 40 | 60 | 139 | 149 | 159 |
| 8 | 30 | 70 | 168 | 155 | 173 |
| 9 | 20 | 80 | 168 | 152 | 159 |
| 10 | — | 100 | 120 | 118 | 121 |

Table C

| Diamine I | : | 2,5-dichloro-1,4-diaminobenzene |
| Diamine II | : | 2-methyl-1,4-diaminobenzene |

| No. | Mol ratio in % I : II | | Relative colour strength in % Polyvinyl-chloride | Alkydmelamine lacquer | Polyurethane |
|---|---|---|---|---|---|
| 1 | 100 | — | 100 | 100 | 100 |
| 2 | 90 | 10 | 105 | 105 | 103 |
| 3 | 80 | 20 | 106 | 110 | 112 |
| 4 | 70 | 30 | 122 | 140 | 148 |
| 5 | 60 | 40 | 131 | 141 | 154 |
| 6 | 50 | 50 | 121 | 131 | 139 |
| 7 | 40 | 60 | 110 | 119 | 116 |
| 8 | 30 | 70 | 129 | 131 | 127 |
| 9 | 20 | 80 | 141 | 141 | 141 |
| 10 | — | 100 | 76 | 105 | 103 |

Table D

| Diamine I | : | 2-chloro-1,4-diaminobenzene |
| Diamine II | : | 2-chloro-5-methyl-1,4-diaminobenzene |

| No. | Mol ratio in % I : II | | Relative colour strength in % Polyvinyl-chloride | Alkydmelamine lacquer | Polyurethane |
|---|---|---|---|---|---|
| 1 | 100 | — | 100 | 100 | 100 |
| 2 | 90 | 10 | 110 | 117 | 113 |
| 3 | 80 | 20 | 130 | 131 | 127 |
| 4 | 70 | 30 | 152 | 153 | 158 |
| 5 | 60 | 40 | 152 | 156 | 160 |
| 6 | 50 | 50 | 152 | 157 | 159 |
| 7 | 40 | 60 | 163 | 174 | 184 |
| 8 | 30 | 70 | 170 | 165 | 170 |
| 9 | 20 | 80 | 160 | 158 | 170 |
| 10 | — | 100 | 115 | 118 | 121 |

What is claimed is:

1. A pigment, being a co-condensate mixture of two compounds of formula I,

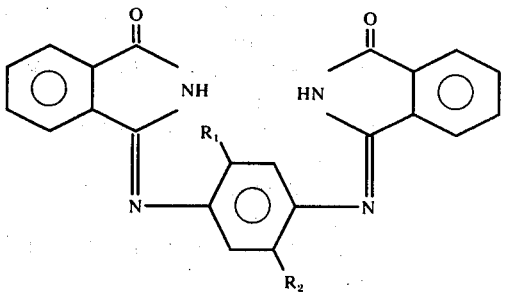

wherein
$R_1$ is chloro, bromo, fluoro, methyl, methoxy or ethoxy, and
$R_2$ is hydrogen or has one of the significances of $R_1$, wherein one of the compounds in said mixture is present in an amount of from 20 to 70 mol % and the other compound in an amount of from 80 to 30 mol %.

2. A pigment according to claim 1, wherein, in the compounds of formula I, $R_1$ is chlorine or methyl.

3. A pigment according to claim 1, wherein, in the compounds of formula I, $R_2$ is hydrogen, chlorine or methyl.

4. A pigment according to claim 1, wherein said mixture consists of a first compound of formula I in which $R_1$ and $R_2$ are chlorine and a second compound of formula I in which $R_1$ is chlorine and $R_2$ is hydrogen.

5. A pigment according to claim 1, wherein said mixture consists of a first compound of formula I in which $R_1$ and $R_2$ are chlorine and a second compound of formula I in which $R_1$ is chlorine and $R_2$ is methyl.

6. A pigment according to claim 1, wherein said mixture consists of a first compound of formula I in which $R_1$ and $R_2$ are chlorine and a second compound of formula I in which $R_1$ is methyl and $R_2$ is hydrogen.

7. A pigment according to claim 1, wherein said mixture consists of a first compound of formula I in which $R_1$ is chlorine and $R_2$ is hydrogen and a second compound of formula I, in which $R_1$ is chlorine and $R_2$ is methyl.

8. A pigment according to claim 1, wherein said mixture consists of a first compound of formula I, in which $R_1$ is chlorine and $R_2$ is hydrogen and a second compound of formula I, in which $R_1$ is methyl and $R_2$ is hydrogen.

9. A pigment according to claim 4, wherein said first compound is present in a mol% of 30 and said second compound in a mol% of 70 of the co-condensate mixture.

* * * * *